US00PP28860P3

(12) United States Plant Patent
Shiobara

(10) Patent No.: US PP28,860 P3
(45) Date of Patent: Jan. 9, 2018

(54) ***HYDRANGEA* PLANT NAMED 'SK2DAMA'**

(50) Latin Name: *Hydrangea macrophylla*
Varietal Denomination: SK2DAMA

(71) Applicant: Shigeo Shiobara, Saitama (JP)

(72) Inventor: Shigeo Shiobara, Saitama (JP)

( * ) Notice: Subject to any disclaimer, the term of this patent is extended or adjusted under 35 U.S.C. 154(b) by 9 days.

(21) Appl. No.: 15/330,175

(22) Filed: Aug. 18, 2016

(65) Prior Publication Data

US 2017/0071088 P1 Mar. 9, 2017

Related U.S. Application Data

(60) Provisional application No. 62/283,728, filed on Sep. 9, 2015.

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Audrey Charles

(57) ABSTRACT

A new and distinct cultivar of *Hydrangea* plant named 'SK2DAMA', characterized by its deep red-purple colored inflorescences, dark green-colored foliage, and moderately vigorous, compact, upright-mounded growth habit, is disclosed.

1 Drawing Sheet

CROSS-REFERENCE TO RELATED APPLICATIONS

This application claims the benefit of U.S. Provisional Application No. 62/283,728 filed Sep. 9, 2015.

Latin name of genus and species of plant claimed: *Hydrangea macrophylla.*

Variety denomination: 'SK2DAMA'.

BACKGROUND OF THE INVENTION

The present invention relates to a new and distinct cultivar of *Hydrangea* plant botanically known as *Hydrangea macrophylla* and hereinafter referred to by the cultivar name 'SK2DAMA'.

The new *Hydrangea* cultivar is a naturally-occurring sport of *Hydrangea macrophylla* 'Dancing Angel', U.S. Plant Pat. No. 20,140, characterized by its pink and red-purple bicolored inflorescences, dark green-colored foliage, and compact, upright-mounded growth habit. The new cultivar was discovered as a side shoot and selected during June 2007 in a controlled environment in Honjo, Japan.

Asexual reproduction of the new cultivar by softwood cuttings since June 2007 in Honjo, Japan has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'SK2DAMA' as a new and distinct cultivar of *Hydrangea* plant:

1. Deep red-purple colored inflorescences;
2. Dark green-colored foliage; and
3. Moderately vigorous, compact, upright-mounded growth habit.

Plants of the new cultivar differ from plants of the parent primarily flower color. The new cultivar is a solid red-purple color while the parent is pink and red-purple bicolored.

Of the many commercially available *Hydrangea* cultivars, the most similar in comparison to the new cultivar is MAGICAL Ruby Red 'Kolmaru', U.S. Plant Pat. No. 25,104. However, in comparison, plants of the new cultivar differ from plants of 'Kolmaru' in at least the following characteristics:

1. Plants of the new cultivar have an inflorescence color that is a different shade of red-purple from plants of 'Kolmaru';
2. Plants of the new cultivar have smaller leaves than plants of 'Kolmaru'; and
3. Plants of the new cultivar are more compact than plants of 'Kolmaru'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'SK2DAMA'. The plants were approximately one-year old and were grown in one-gallon containers for approximately 7 months in a poly-covered greenhouse in West Chicago, Ill. Plants were given one pinch at transplant.

DETAILED BOTANICAL DESCRIPTION

Figure 1:
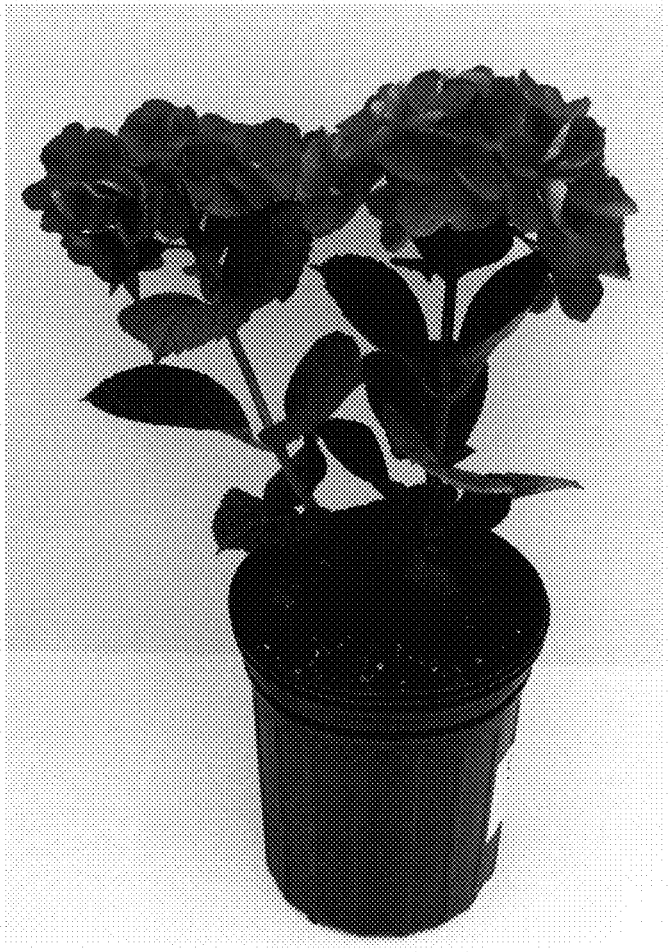
FIG. 1 illustrates a side view of the overall growth and flowering habit of 'SK2DAMA'.
Figure 2:
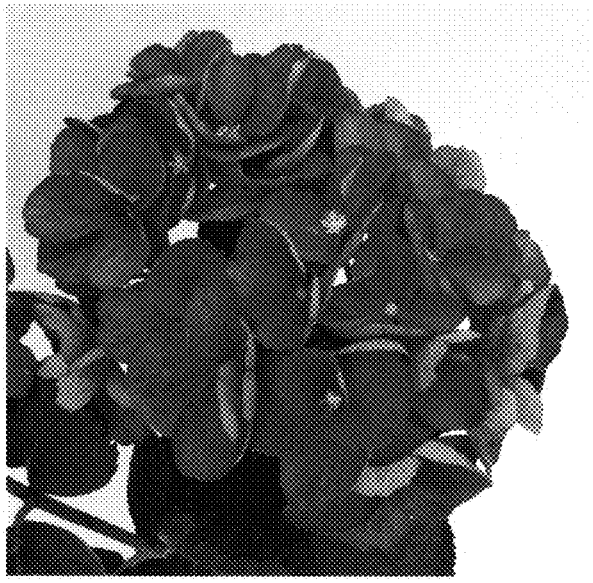
FIG. 2 illustrates a close-up view of an individual inflorescence of 'SK2DAMA'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2016 under natural light conditions in West Chicago, Ill.

The following descriptions and measurements describe approximately one-year old plants produced from softwood cuttings from stock plants and grown under conditions comparable to those used in commercial practice. Plants were not grown in acidic conditions. It is known that the inflorescences do not turn blue with aluminum sulfate treatments. The plants were grown in one-gallon containers for approximately 7 months in a poly-covered greenhouse in West Chicago, Ill. Plants were given one pinch at transplant. During winter months supplemental heat was provided to maintain temperatures above a minimum of 38° F. (3.3° C.). No supplemental lighting was provided. Measurements and numerical values represent averages of typical plants.

Botanical classification: *Hydrangea macrophylla* cultivar SK2DAMA.

Parentage:

*Parent*.—'Dancing Angel', U.S. Plant Pat. No. 20,140.

Propagation:

*Type cutting*.—Softwood.

*Time to initiate roots*.—Approximately 15 to 20 days.

*Time to produce a rooted cutting*.—Approximately 25 to 30 days.

*Root description*.—Medium thickness, fleshy, creamy yellow 11D in color.

*Rooting habit*.—Moderate branching, moderately dense.

Plant description:

*Commercial crop time*.—Approximately 14 to 16 weeks from a rooted cutting to finish in an 18 cm pot.

*Growth habit and general appearance*.—Deciduous shrub, moderately vigorous, compact, upright-mounded.

*Hardiness*.—USDA Zone 5 (−20° F. to −15° F.).

*Heat tolerance*.—Regularly tolerates temperatures as high as 38° C. in the summer.

*Size*.—Height from soil level to top of plant plane: Approximately 32.0 cm. Width: Approximately 34.0 cm.

*Branching habit*.—Freely branching. Pinching enhances branching. Quantity of lateral branches per plant: Approximately 2.

*Branch*.—Shape: Rounded. Strength: Strong. Length to base of inflorescence: Approximately 24.0 cm. Diameter: Approximately 5.0 mm. Length of central internode: Approximately 5.5 cm. Texture of young stem: Glabrous. Texture of mature stem: Glabrous. Color of young stem: 144A. Color of mature stem: 144A, with age becoming woody 200A.

*Lenticels*.—Quantity per internode: Approximately 28. Shape: Round to elliptic. Size: Approximately 0.5 mm to 3.0 mm. Color: N77A.

Foliage description:

*General description*.—Quantity of leaves per lateral branch: Approximately 10. Fragrance: None detected. Form: Simple. Arrangement: Opposite.

*Leaves*.—Shape: Elliptic. Margin: Serrated. Apex: Acuminate. Base: Rounded. Venation pattern: Pinnate. Length of mature leaf: Approximately 9.0 cm. Width of mature leaf: Approximately 7.0 cm. Texture of upper and lower surfaces: Coriaceous, glabrous. Color of upper surface of young foliage: Closest to NN137B with an overlay of and margins of 187A venation of 145A. Color of lower surface of young foliage: Closest to 147B with venation of 146D. Color of upper surface of mature foliage: Closest to NN137A with a heavy overlay of 187A venation of 145A. Color of lower surface of mature foliage: Closest to 147B with venation of 146D.

*Petiole*.—Length: Approximately 1.6 cm. Diameter: Approximately 3.0 mm. Texture: Glabrous. Color: 146D.

Flowering description:

*Flowering habit*.—Seasonal, May through August.

*Lastingness of individual inflorescence on the plant*.—Approximately 1.5 months.

Inflorescence description:

*General description*.—Type: Single sterile florets arranged on terminal mophead-type panicle, fertile florets senesce before opening, reproductive parts lacking an ovary occasionally observed on sterile florets. Quantity per plant: Approximately 2. Fragrance: None detected. Aspect: Facing upward and outward. Height: Approximately 10.0 cm. Width: Approximately 16.0 cm. Quantity of sterile florets per inflorescence: Approximately 32.

*Peduncle*.—Strength: Strong. Shape: Rounded. Length: Approximately 3.7 cm. Diameter: Approximately 3.0 mm. Texture: Pubescent with appressed hairs. Color: 144A.

Floret description:

*General description*.—Type: Single, sterile.

*Sterile florets, bud just before opening*.—Shape: Globular. Diameter: Approximately 1.5 mm. Color: 145A.

*Sterile florets*.—Depth: Approximately 1.0 cm. Diameter: Approximately 4.8 cm. Corolla: 4 petals, occasionally closed forming a central eye. Shape: Rotate, cruciform. Diameter: Approximately 1.0 cm. Calyx: 4 sepals. Shape: Rotate, cruciform. Diameter: Approximately 4.8 cm.

*Petals, sterile florets*.—Shape: Ovate when open, otherwise petals form a center eye of up to 3.0 mm in diameter and 75B in color. Margin: Entire. Apex: Acute. Base: Truncate. Length: Approximately 5.0 mm. Width: Approximately 2.0 mm. Texture of upper and lower surfaces: Glabrous. Color of upper and lower surfaces: NN155D with an overlay of 75A.

*Sepals, sterile florets*.—Shape: Broadly obovate. Margin: Irregularly scalloped. Apex: Rounded. Base: Attenuate. Length: Approximately 2.3 cm. Width: Approximately 2.5 cm. Texture of upper and lower surfaces: Glabrous. Color of upper surface when first open: Base and centers of 145A, margins of 60C. Color of lower surface when first open: Base and centers of 145C, margins of 60D. Color of upper surface when fully open: 59A to 59B tinted with 71A. Color of lower surface when fully open: 186C.

*Pedicel, sterile florets*.—Strength: Strong. Aspect: Approximately 45° from peduncle axis. Length:

Approximately 2.5 cm. Diameter: Approximately 2.0 mm. Texture: Sparsely pubescent with appressed hairs. Color: 137B with a heavy overlay of 186B.

*Reproductive organs*.—Observed occasionally in the center of sterile florets, ovary lacking. Androecium: Stamen quantity: Approximately 10 per floret. Stamen length: Approximately 4.0 mm. Filament color: NN155D. Anther shape: Kidney-shaped, basally attached. Anther length: Approximately 1.0 mm. Anther color: NN155A. Pollen amount: Sparse. Pollen color: NN155D. Gynoecium: Pistil quantity: 1 per floret. Pistil length: Approximately 2.0 mm. Stigma shape: Round. Stigma color: NN155D. Style length: Approximately 2.0 mm, three-lobed. Style color: NN155D with a faint overlay of 75A.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'SK2DAMA', substantially as herein illustrated and described.

* * * * *